United States Patent
Kim et al.

(10) Patent No.: US 11,328,394 B1
(45) Date of Patent: May 10, 2022

(54) APPARATUS AND METHOD FOR CONTRAST AMPLIFICATION OF CONTRAST-ENHANCED CT IMAGES BASED ON DEEP LEARNING

(71) Applicants: ClariPI Inc., Seoul (KR); Seoul National University R&DB Foundation, Seoul (KR)

(72) Inventors: Jong Hyo Kim, Seoul (KR); Hyun Sook Park, Seoul (KR); Tai Chul Park, Seoul (KR); Chul Kyun Ahn, Seoul (KR)

(73) Assignees: CLARIPI INC., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/380,429

(22) Filed: Jul. 20, 2021

Related U.S. Application Data (63) Continuation of application No. PCT/KR2021/001363, filed on Feb. 2, 2021.

(30) Foreign Application Priority Data

Feb. 1, 2021 (KR) .................. 10-2021-0014378

(51) Int. Cl.
  *G06T 5/00* (2006.01)
  *G06T 5/50* (2006.01)
  *G06N 20/00* (2019.01)

(52) U.S. Cl.
  CPC ............ *G06T 5/009* (2013.01); *G06N 20/00* (2019.01); *G06T 5/50* (2013.01); *G06T 2207/10081* (2013.01); *G06T 2207/20081* (2013.01)

(58) Field of Classification Search
  CPC . G06T 5/009; G06T 5/50; G06T 2207/10081; G06T 2207/20081; G06N 20/00
  See application file for complete search history.

(56) References Cited

U.S. PATENT DOCUMENTS

| | | | |
|---|---|---|---|
| 7,120,276 B1* | 10/2006 | Brady | G06K 9/6206 382/107 |
| 8,149,299 B2* | 4/2012 | Ohwaki | G06T 5/004 348/241 |

(Continued)

FOREIGN PATENT DOCUMENTS

| | | |
|---|---|---|
| JP | 2019005557 | 1/2019 |
| KR | 20190058285 | 5/2019 |

(Continued)

OTHER PUBLICATIONS

International Search Report—PCT/KR2021/001363 dated Oct. 27, 2021.

*Primary Examiner* — Xuemei G Chen
(74) *Attorney, Agent, or Firm* — Cantor Colburn LLP

(57) ABSTRACT

Provided is a deep learning based contrast-enhanced (CE) CT image contrast amplifying method and the deep learning based CE CT image contrast amplifying method includes extracting at least one component CT image between a CE component and a non-CE component for an input CE CT image with the input CE CT image as an input to a previously trained deep learning model; and outputting a contrast-amplified CT image with respect to the CE CT image based on the input CE CT image and the at least one extracted component CT image.

10 Claims, 5 Drawing Sheets

(56) References Cited

U.S. PATENT DOCUMENTS

| | | | | |
|---|---|---|---|---|
| 2004/0131117 | A1* | 7/2004 | Sheraizin | H04N 19/154 |
| | | | | 375/240.12 |
| 2008/0050031 | A1* | 2/2008 | Itoh | G06T 5/20 |
| | | | | 382/260 |
| 2009/0080741 | A1* | 3/2009 | Shinagawa | G06K 9/4609 |
| | | | | 382/131 |
| 2010/0198054 | A1 | 8/2010 | Ewing et al. | |
| 2014/0348428 | A1* | 11/2014 | Lee | G06T 5/40 |
| | | | | 382/169 |
| 2016/0180525 | A1* | 6/2016 | Reynolds | G06T 5/009 |
| | | | | 382/131 |
| 2016/0321790 | A1* | 11/2016 | Wang | G06T 5/40 |
| 2018/0279983 | A1* | 10/2018 | Ohishi | A61B 6/486 |
| 2019/0033409 | A1* | 1/2019 | Huang | G06T 11/008 |
| 2019/0108634 | A1* | 4/2019 | Zaharchuk | G06T 7/0012 |
| 2019/0122348 | A1* | 4/2019 | Jensen | G06T 5/009 |
| 2020/0143571 | A1* | 5/2020 | Bagherzadeh | G06T 11/003 |
| 2020/0242741 | A1* | 7/2020 | Liu | G06T 7/174 |
| 2020/0294288 | A1* | 9/2020 | Smith | G16H 50/20 |
| 2020/0367844 | A1* | 11/2020 | Dang | A61B 6/482 |
| 2021/0158139 | A1* | 5/2021 | Mai | G06T 5/50 |
| 2021/0224957 | A1* | 7/2021 | Iwase | G06T 7/0012 |

FOREIGN PATENT DOCUMENTS

| | | |
|---|---|---|
| KR | 20190137283 | 12/2019 |
| KR | 20200026071 | 3/2020 |
| KR | 20200063222 | 6/2020 |

\* cited by examiner

APPARATUS AND METHOD FOR CONTRAST AMPLIFICATION OF CONTRAST-ENHANCED CT IMAGES BASED ON DEEP LEARNING

BACKGROUND

Field

The present disclosure relates to an apparatus and a method for amplifying the contrast of a contrast-enhanced CT (CE CT) image based on deep learning.

Description of the Related Art

When computed tomographic scanning (CT) is used, a subject enters a large circular machine with an X-ray generator to be scanned so that a cross-sectional image intersecting a human body may be obtained. It has an advantage in that structures are less overlaid than in simple X-ray imaging so that structures and lesions can be more clearly observed. Therefore, CT is being widely utilized for a complete check-up for most organs and diseases.

The contrast of CT images can be said to be very important to precisely diagnose lesions, and therefore efforts to acquire a high contrast image from a CT image are continuing together with the development of the CT examination methods. Generally, the lesion has a characteristic in that vascularity is higher or lower than the other surrounding tissues. Therefore, when a CT scanning is performed after injecting a contrast medium which increases an X-ray attenuation degree of a blood vessel, the image contrast between the lesion and the surrounding tissue becomes clearer. In clinical practice, contrast enhancement CT exam (with a contrast medium injection) is utilized as an important exam method for acquiring an image with an improved contrast of a lesion.

However, most of the efforts of the related art for amplifying the contrast of the CT image require an injection of a large amount of contrast media, which potentially causes patient hazard. Specifically, when the recent concern on the risk of the contrast media is considered, the efforts for acquiring a high quality diagnostic image need to be accompanied by efforts for minimizing the amount of contrast media injection.

As an example of such efforts, CT (computed tomography) manufacturers are releasing CT systems including a dual energy scanning function. The dual energy CT may improve the image contrast for contrast media component so that it is possible to reduce an injection amount of contrast media. However, the dual energy CT system of the related art is more expensive than the existing products, and as such it is difficult to be generally supplied. In addition, the degree of improvement of image contrast by the dual energy is limited, and therefore it cannot be a true solution and a new solution is required. That is, it is required to develop a more effective technique to acquire a high-quality diagnostic image (a high contrast CT image) while minimizing the amount of contrast media injection.

In the meantime, the deep learning technology is a new type of computing technique which achieves a specific purpose using a general-purpose program code which can be trained according to a given learning data set, instead of coding a series of detailed programs and its excellent performance is recognized in various image processing fields.

However, in order to show the desirable performance of the deep learning model, it is not only required to ensure enough training data sets, but also it needs to be accompanied by a method of partitioning data to allow the deep learning model to be trained for data in a previously designated range and to be operated for data in the previously designated range even in an actual usage stage. In order to apply the deep learning to medical images in which safety is particularly important, it can be said that the development of the effective deep learning training technology which satisfies such prerequisites is even more important.

A background art of the present disclosure is disclosed in Korean Unexamined Patent Application Publication No. 10-2020-0026071.

SUMMARY

The present disclosure has been made an effort to solve the problems of the related art and the object thereof is to provide an apparatus and a method for amplifying the image contrast of a CE CT image based on deep learning which are capable of achieving a high-quality diagnostic image (CT image) while minimizing the amount of contrast medium injection.

The present disclosure has been made an effort to solve the problems of the related art and the object thereof is to provide a training (learning) method of a deep learning model by means of an apparatus for amplifying the image contrast of a CE CT image based on deep learning to more effectively apply the deep learning to medical images in which the safety is specifically important.

The present disclosure has been made an effort to solve the problems of the related art and the object thereof is to provide an apparatus and a method for amplifying the image contrast of a CE CT image based on deep learning and a training method of a deep learning model therethrough which ensure the performance and the safety of the deep learning while utilizing the advantages of the deep learning.

However, technical objects to be achieved by the embodiment of the present disclosure are not limited to the technical objects as described above and other technical objects may be present.

As a technical means to achieve the above-described technical object, according to an aspect of the present disclosure, a deep learning based CE CT image contrast amplifying method includes: extracting at least one component CT image either a contrast enhancement (CE) component or a non-contrast enhancement (non-CE) component from an input CE CT image with the input CE CT image as an input to a previously trained deep learning model; and outputting a contrast-amplified CT image with respect to the input CE CT image based on the input CE CT image and the said at least one extracted component CT image.

Further, according to an aspect of the present disclosure, a deep learning based CE CT image contrast amplifying method may further include before the said extracting of at least one component CT image: extracting exam information from an input CE CT image; and selecting at least one deep learning model corresponding to the exam information among a plurality of previously trained deep learning models, and the extracting of at least one component CT image may include extracting at least one component CT image with respect to the input CE CT image with the input CE CT image as an input to the said at least one selected deep learning model.

In the deep learning based CE CT image contrast amplifying method according to one aspect of the present disclosure, the outputting of a contrast-amplified CT image may include: multiplying the input CE CT image and at least one component CT image by each predetermined ratio, respectively, followed by summing of the multiplied results.

In the deep learning based CE CT image contrast amplifying method according to one aspect of the present disclosure, the outputting of a contrast-amplified CT image may include: generating a first CT image and a second CT image by multiplying the input CE CT image and at least one component CT image by each predetermined ratio, respectively, followed by summing of the multiplied results; and outputting a composite color image by applying a predetermined color tone table to the first and the second CT images.

Further, according to one aspect of the present disclosure, a deep learning based CE CT image contrast amplifying method may further include before the extracting of at least one component CT image: composing at least one component CT image dataset based on the image pairs of a first training CT dataset; generating a second training CT dataset based on the said at least one composed component CT image dataset and the first training CT dataset; and generating and training a deep learning model to be trained, in advance, using the second training CT dataset to extract at least one component CT image, and the said previously trained deep learning model may be a deep learning model which is trained by the training.

Further, the deep learning based CE CT image contrast amplifying method according to one aspect of the present disclosure may further include before the extracting of exam information: composing at least one component CT image dataset based on the image pairs of a first training CT dataset; generating a second training CT dataset consisting of image pairs each based on the said at least one composed component CT image and an original image of the said first training CT dataset; extracting exam information from the second training CT dataset and grouping the second training CT dataset into a plurality of groups according to a predetermined rule; and generating and training of a plurality of deep learning models to be trained such that each deep learning model to be trained may correspond to each group of the second training CT dataset, and the said plurality of previously trained deep learning models considered in the said selecting may be the plurality of deep learning models to be trained which is trained by the said generating and training.

In the meantime, according to another aspect of the present disclosure, a deep learning based CE CT image contrast amplifying apparatus may include: an image extracting unit which extracts at least one component CT image with respect to an input CE CT image with the input CE CT image as an input to a previously trained deep learning model; and an amplified image output unit which outputs a contrast-amplified CT image based on at least one extracted component CT image and the input CE CT image.

Further, the deep learning based contrast-enhanced image contrast amplifying apparatus may further include: an exam information extracting unit which extracts exam information from an input CE CT image; and a deep learning model selecting unit which selects at least one deep learning model corresponding to the exam information among a plurality of previously trained deep learning models, and the said image extracting unit may input the input CE CT image to at least one deep learning model selected by the exam information extracting unit and the deep learning model selecting unit to extract at least one component CT image with respect to the input CE CT image.

In the deep learning based CE CT image contrast amplifying apparatus, according to an aspect of the present disclosure, the image output unit may multiply the input CE CT image and at least one component CT image by each predetermined ratio, respectively, followed by summing of the multiplied results to produce output.

In the deep learning based CE CT image contrast amplifying apparatus, according to an aspect of the present disclosure, the amplified image output unit may multiply the input CE CT image and at least one component CT image by each predetermined ratio, respectively, followed by summing of the multiplied results to generate a first CT image and a second CT image, respectively, and apply a predetermined color tone table to the said first and second CT images to output a composed color image.

Further, the deep learning based CE CT image contrast amplifying apparatus may further include: a deep learning training unit which generates and trains a plurality of deep learning models to be trained, the deep learning training unit composes at least one component CT image dataset based on image pairs of a first training CT dataset; generates a second training CT dataset consisting of image pairs each based on the said at least one composed component CT image and an original image of the said first training CT dataset; and generates and trains a deep learning model to be trained, in advance, using the second training CT dataset to extract at least one component CT image, and the previously trained deep learning model may be a deep learning model which is trained by the training.

Further, the deep learning based CE CT image contrast amplifying apparatus may further include: a deep learning group training unit which generates and trains a plurality of deep learning models to be trained, wherein the deep learning group training unit composes at least one component image dataset based on image pairs of a first training CT dataset; generates a second training CT dataset consisting of image pairs each based on at least one composed component CT image and an original image of the first training CT dataset; and extracts exam information from the second training CT dataset and groups the second training CT dataset into a plurality of groups according to a predetermined rule, and generates and trains a plurality of deep learning models to be trained such that each deep learning model to be trained may correspond to each group of the second training CT dataset, and the plurality of previously trained deep learning models may be the plurality of deep learning models to be trained which is trained by the deep learning group training unit.

The above-described solving means are merely illustrative but should not be construed as limiting the present disclosure. In addition to the above-described embodiments, additional embodiments may be further provided in the drawings and the detailed description of the present disclosure.

According to the above-described solving means of the present disclosure, the contrast of the CT image is amplified based on deep learning to acquire a high-quality diagnostic image (CT image) while minimizing the amount of a contrast medium injection.

According to the above-described solving means of the present disclosure, the plurality of deep learning models (a plurality of deep learning models to be trained) is trained according to the exam information of the CT image to effectively apply the deep learning to a medical image in which the safety is specifically important.

According to the above-described solving means of the present disclosure, an apparatus and a method for amplifying a contrast of a CE CT image based on deep learning, and a deep learning model training (learning) method therethrough which ensure the performance of the deep learning and secure the safety while utilizing the advantages of the deep learning may be provided.

However, the effect which can be achieved by the present disclosure is not limited to the above-described effects and there may be other effects.

BRIEF DESCRIPTION OF DRAWINGS

The above and other aspects, features and other advantages of the present disclosure will be more clearly understood from the following detailed description taken in conjunction with the accompanying drawings, in which.

DETAILED DESCRIPTION OF THE EMBODIMENT

Hereinafter, the present disclosure will be described more fully hereinafter with reference to the accompanying drawings, in which exemplary embodiments of the present disclosure are shown. However, the present disclosure can be realized in various different forms, and is not limited to the embodiments described herein. Accordingly, in order to clearly explain the present disclosure in the drawings, portions not related to the description are omitted. Like reference numerals designate like elements throughout the specification.

Throughout this specification and the claims that follow, when it is described that an element is "coupled" to another element, the element may be "directly coupled" to the other element or "electrically coupled" or "indirectly coupled" to the other element through a third element.

Through the specification of the present disclosure, when one member is located "on", "above", "on an upper portion", "below", "under", and "on a lower portion" of the other member, the member may be adjacent to the other member or a third member may be disposed between the above two members.

In the specification of the present disclosure, unless explicitly described to the contrary, the word "comprise" and variations such as "comprises" or "comprising", will be understood to imply the inclusion of stated elements but not the exclusion of any other elements.

In the present disclosure, a CE CT image (CT image) may also be referred to as CT data or a medical image.

Figure 1:
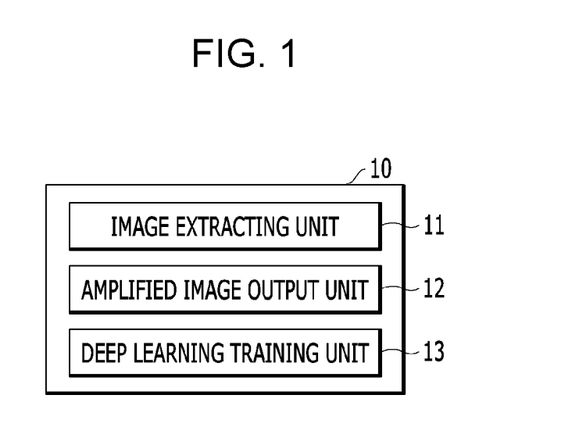
FIG. 1 is a view illustrating a schematic configuration of a deep learning based CE CT image contrast amplifying apparatus according to an exemplary embodiment of the present disclosure.

FIG. 1 is a view illustrating a schematic configuration of a deep learning based CE CT image contrast amplifying apparatus according to an exemplary embodiment of the present disclosure. Hereinafter, the deep learning based CE CT image contrast amplifying apparatus 10 according to an exemplary embodiment of the present disclosure is referred to as this apparatus 10 for the convenience of description.

Referring to FIG. 1, this apparatus 10 may include an image extracting unit 11, an amplified image output unit 12, and a deep learning training unit 13. However, the configuration of this apparatus 10 is not limited thereto. For example, this apparatus 10 may include a database (not illustrated) in which CT images acquired by a computed tomography (CT), a magnetic resonance imaging (MRI) device, a positron emission tomography (PET), and the like are stored.

According to an exemplary embodiment of the present disclosure, the image extracting unit 11 may input an input CE CT image to a previously trained deep learning model to extract at least one component CT image of a CE component and a non-CE component as a learning result of a deep learning model.

The input CE CT image may be an image acquired by computed tomography (CT), magnetic resonance imaging (MRI), or positron emission tomography (PET), but is not limited thereto and may be an image acquired by various imaging devices.

According to this, this apparatus 10 may include a deep learning model which has been trained in advance. Here, the deep learning model is a deep learning model which has been trained in advance by the deep learning training unit 13 to be described below and may specifically refer to a deep learning model which has been trained to output at least one component CT image with respect to a CE CT image which is input to the deep learning model.

When the deep learning model is described in the present disclosure, a deep learning model before being trained by the deep learning training unit 13 may be referred to as a deep learning model to be trained. According to this, after completing the training for the deep learning model to be trained, the deep learning model means a previously trained deep learning model. In other words, the previously trained deep learning model considered in the image extracting unit 11 may refer to a deep learning model to be trained which has been trained by the deep learning training unit 13. The training of the deep learning model to be trained will be described in more detail below.

According to an exemplary embodiment of the present disclosure, the amplified image output unit 12 may output a contrast-amplified CT image based on at least one extracted component CT image and the input CE CT image. In other words, the amplified image output unit 12 multiplies at least one component CT image and the input CE CT image by each predetermined ratio, respectively, followed by summing of the multiplied results to output a contrast-amplified CT image with respect to the input CE CT image.

According to another exemplary embodiment, the amplified image output unit 12 multiplies the input CE CT image and at least one component CT image by each predetermined ratio, respectively, followed by summing of the multiplied results to generate a first CT image and a second CT image, and applies a predetermined color tone table to the said first and second CT images to output a composed color image.

According to an exemplary embodiment of the present disclosure, the deep learning training unit 13 may generate and train a deep learning model to be trained. The deep learning training unit 13 may generate and train the deep learning model to be trained before extracting at least one component CT image from the input CE CT image by the image extracting unit 11.

Hereinafter, the deep learning training unit 13 will be described in more detail.

According to an exemplary embodiment of the present disclosure, the deep learning training unit 13 may train the deep learning model to be trained using a CT data set for training (in other words, a CT data set for deep learning training) before extracting at least one component CT image from the input CE CT image by the image extracting unit 11.

Further, the deep learning training unit 13 may compose at least one component CT image from an image pair of the first training CT dataset, before training the deep learning model to be trained. Further, the deep learning training unit 13 may generate a second training CT dataset based on the dataset of the said at least one composed component CT image and the first training CT dataset. Next, the deep learning training unit 13 may train the deep learning model to be trained using the generated second training CT dataset.

According to an exemplary embodiment of the present disclosure, the original image of the first training CT dataset may be configured by a pair of CT images scanned before and after injecting the contrast medium (pre- and post-contrast CT image pair). In this case, the deep learning training unit 13 may compose a CE component CT image based on the said the pre- and post-contrast CT image pair.

According to an exemplary embodiment, the deep learning training unit 13 may compose the CE component CT image by subtracting the post-contrast CT image from the pre-contrast CT image.

At this time, the deep learning training unit 13 may use the pre-contrast CT image as a non-CE component CT image.

Additionally, the deep learning training unit 13 may apply a motion compensating operation between the pre- and post-contrast CT image pair according to predetermined criteria (a predetermined method).

According to still another exemplary embodiment of the present disclosure, the original image of the first training CT dataset may be configured by a low energy CT image and a high energy CT image obtained from a CT scanned after injecting a contrast medium using a CT device having a dual energy scanning function. At this time, the deep learning training unit 13 may compose the CE component CT image based on the low energy CT and high energy CT image pair.

The deep learning training unit 13 may compose the CE component CT image by multiplying the low energy CT image and the high energy CT image by each predetermined ratio, respectively, followed by summing of the multiplied results.

Further, the deep learning training unit 13 may compose a non-CE component CT image by multiplying the low energy CT image and the high energy CT image by another each predetermined ratio, respectively, followed by summing of the multiplied results.

Further, the deep learning training unit 13 may generate at least one composite low contrast CT image by multiplying the composed CE component CT image by at least one predetermined ratio, followed by adding the multiplied result to the composed non-CE component CT image.

As described above, the deep learning training unit 13 may generate a second training CT dataset configured by at least one composite low contrast CT image and at least one component CT image of a composite CE component and a composite non-CE component, based on the CT image pair of the first training CT dataset.

Further, the deep learning training unit 13 may generate the deep learning model to be trained before extracting at least one component CT image from the input CE CT image by the image extracting unit 11. Further, the deep learning training unit 13 may generate a second training CT dataset to which at least one component CT image composed based on the CT image pair of the first training CT dataset and at least one composite low contrast CT image are added, so as to allow the deep learning model to be trained to have a function of extracting at least one component CT image from the CE CT image input thereto. Further, the deep learning training unit 13 may enter each composite low contrast CT image in the second training CT dataset as an input to the deep learning model to be trained, and repeatedly train the deep learning model to be trained, so as to minimize the difference between the at least one composed component CT image and the output of the deep learning model to be trained.

Figure 2:
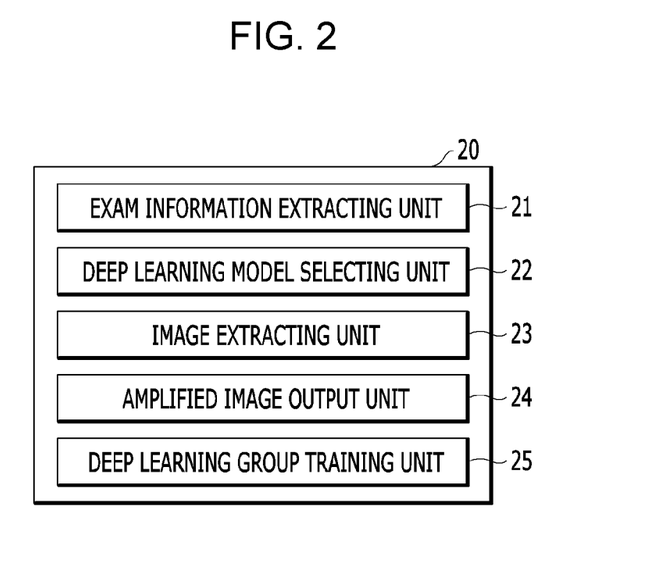
FIG. 2 is a view illustrating a schematic configuration of a deep learning based CE CT image contrast amplifying apparatus according to another exemplary embodiment of the present disclosure.

FIG. 2 is a view illustrating a schematic configuration of a deep learning based CE CT image contrast amplifying apparatus according to another exemplary embodiment of the present disclosure.

Hereinafter, an image extracting unit 23 and an amplified image output unit 24 of this apparatus 20 which will be described with reference to FIG. 2 may be the same or correspond to the image extracting unit 11 and the amplified image output unit 12 of this apparatus 10 which has been described above based on FIG. 1. Accordingly, even though omitted below, the description for the image extracting unit 11 and the amplified image output unit 12 may be applied to the description for the image extracting unit 23 and the amplified image output unit 24 in the same manner.

Referring to FIG. 2, this apparatus 20 may include an exam information extracting unit 21, a deep learning model selecting unit 22, an image extracting unit 23, an amplified image output unit 24, and a deep learning group training unit 25.

The exam information extracting unit 21 may extract exam information from an input CT image. The exam information may include body part information and scan attribute information of the CT image.

Here, the body part information may refer to information about an organ portion. That is, the body part information refers to information about the organs of the human body of major interest, and may refer to, for example, information about organs such as head, chest, and abdomen. Further, the scan attribute information refers to information about CT scanning variables, for example, may refer to information such as a reconstruction kernel, a tube voltage, a tube current, and a slice thickness.

According to an exemplary embodiment of the present disclosure, the exam information extracting unit 21 may extract exam information from header information included in the input CT image.

According to another exemplary embodiment, the exam information extracting unit 21 may extract exam information by inputting the input CT image to a predetermined classifier. In this case, the predetermined classifier may extract one or more predetermined image features from the input CT image and allocate the image features to one of the predetermined number of categories.

The deep learning model selecting unit 22 may select at least one deep learning model corresponding to the exam information extracted by the exam information extracting unit 21, among a plurality of previously trained deep learning models.

Further, the deep learning model selecting unit 22 may apply a predetermined rule to the exam information extracted by the exam information extracting unit 21 to select at least one (one or more) deep learning model corresponding to the exam information extracted by the exam information extracting unit 21, among the plurality of previously trained deep learning models.

According to an exemplary embodiment of the present disclosure, the image extracting unit 23 may extract at least one component CT image with respect to the input CE CT image with the input CE CT image as an input to at least one deep learning model selected by the deep learning model selecting unit 22.

According to an exemplary embodiment of the present disclosure, the amplified image output unit 24 may output a contrast-amplified CT image based on at least one extracted component CT image and the input CE CT image.

According to this, this apparatus 20 may include a plurality of deep learning models. Here, each of the plurality of deep learning models is a deep learning model which has been trained in advance by the deep learning group training unit 25 to be described below and may specifically refer to a deep learning model which has been trained to output at least one component CT image with respect to an input CE CT image.

The plurality of deep learning models considered in this apparatus 20 may be generated by the deep learning group training unit 25. The deep learning group training unit 25 may generate a plurality of deep learning models according to the exam information. In other words, the deep learning group training unit 25 may generate and train the plurality of deep learning models to be trained. Specifically, the deep learning group training unit 25 may generate a plurality of deep learning models according to a combination of the body part information and the scan attribute information of the CT image included in the exam information.

In other words, this apparatus 20 may include a plurality of deep learning models generated according to the exam information (according to the combination of the body part information and the scan attribute information). The plurality of deep learning models generated according to the combination of the body part information and the scan attribute information may be trained by the deep learning group training unit 25 using each CT data set for training (that is, a CT data set for deep learning training) grouped according to the combination of the body part information and the scan attribute information.

When the deep learning model is described in the present disclosure, a deep learning model before being trained by the deep learning group training unit 25 may be referred to as a deep learning model to be trained. According to this, after completing the training for the deep learning model to be trained, the deep learning model means a previously trained deep learning model. In other words, the plurality of previously trained deep learning models considered in the deep learning model selecting unit 22 may refer to a plurality of deep learning models to be trained which has been trained by the deep learning group training unit 25. The training of the deep learning model to be trained will be described in more detail below.

According to another exemplary embodiment of the present disclosure, the deep learning model selecting unit 22 may select at least one deep learning model corresponding to the exam information extracted by the exam information extracting unit 21 (corresponding to a combination of the body part information and the scan attribute information extracted by the exam information extracting unit 21), among the plurality of deep learning models which is generated according to the exam information (according to the combination of the body part information and the scan attribute information) to be trained in advance.

The deep learning model selecting unit 22 may select at least one deep learning model which is suitable to apply an input CE CT image, among a plurality of previously trained deep learning models, based on the exam information extracted by the exam information extracting unit 21.

For example, it is assumed that the input CE CT image is an abdomen CT image which is a CT image of a first body part (for example, an abdomen) which is reconstructed by a first scan attribute (for example, a scan attribute of a low dose and a thick slice). In this case, the deep learning model selecting unit 22 may select a single deep learning model (for example, a first deep learning model) trained with training data (a CT data set for training) in which a body part is an abdomen and a scan attribute is a low dose and a thick slice, as a deep learning model corresponding to the first scan attribute and the first body part, among the plurality of previously trained deep learning models.

As another example, it is assumed that the input CE CT image is an abdomen CT image which is a CT image of a first body part (for example, an abdomen) which is reconstructed by a second scan attribute (for example, a scan attribute of an ultra-low dose and a thin slice). In this case, the deep learning model selecting unit 22 may select a single deep learning model (for example, a second deep learning model) trained with training data (a CT data set for training) in which a body part is an abdomen and a scan attribute is an ultra-low dose and a thin slice, as a deep learning model corresponding to the second scan attribute and the first body part, among the plurality of previously trained deep learning models.

As still another example, it is assumed that the input CE CT image is a chest CT image which is a CT image of a second body part (for example, a chest) reconstructed by applying a third scan attribute (for example, a reconstruction kernel with a high sharpness as a first sharpness is applied to a lung area) to a first area and applying a fourth scan attribute (for example, a reconstruction kernel with a low sharpness as a second sharpness is applied to a soft tissue area) to a second area. In this case, the deep learning model selecting unit 22 may select two deep learning models including a third deep learning model corresponding to the third scan attribute and the second body part and a fourth deep learning model corresponding to the fourth scan attribute and the second body part, among the plurality of previously trained deep learning models. Specifically, the deep learning model selecting unit 22 may select two deep learning models including the third deep learning model which is trained with training data (a CT data set for training) in which a body part is a chest and a reconstruction kernel has a high sharpness and the fourth deep learning model which is trained with training data (a CT data set for training) in which a body part is a chest and a reconstruction kernel has a low sharpness, among the plurality of previously trained deep learning models.

As described above, the deep learning model selecting unit 22 may select one or more deep learning models (that is, at least one deep learning model) among the plurality of previously trained deep learning models in consideration of the combination of the body part information and the scan attribute information included in the extracted exam information, based on the exam information extracted by the exam information extracting unit 21.

The amplified image output unit 24 allows at least one selected deep learning model to extract at least one component CT image from the input CE CT image with the input CE CT image as an input of at least one deep learning model selected by the deep learning model selecting unit 22, and outputs a contrast-amplified CT image by multiplying the input CE CT image and at least one extracted component CT image by each predetermined ratio, respectively, followed by summing of the multiplied results.

As an example, it is assumed that a deep learning model selected by the deep learning model selecting unit 22 is a single (one) deep learning model. In this case, the amplified image output unit 24 inputs the input CE CT image to the single deep learning model selected by the deep learning model selecting unit 22 to allow the single deep learning model to extract at least one component CT image from the input CE CT image, and outputs a contrast-amplified CT image by multiplying the input CE CT image and at least one extracted component CT image by each predetermined ratio, respectively, followed by summing of the multiplied results.

As another example, it is assumed that the deep learning model selected by the deep learning model selecting unit 22 is a plurality of deep learning models. In this case, the amplified image output unit 24 inputs the input CE CT image to a plurality of deep learning models selected by the deep learning model selecting unit 22 to allow each of the plurality of deep learning models to extract a CE component CT image from the CE CT image input thereto, and outputs a contrast-amplified CT image by multiplying the input CE CT image and a plurality of at least one component CT image extracted by the plurality of deep learning models by each predetermined ratio, respectively, followed by summing of the multiplied results.

At this time, the amplified image output unit 24 may generate a first and second CT images by multiplying the input CE CT image and at least one component CT image by each predetermined ratio, respectively, and output a composed color image by applying a predetermined color tone table to the said first and second CT images.

The deep learning group training unit 25 may generate and train a plurality of deep learning models to be trained, before extracting exam information from the input CE CT image by the exam information extracting unit 21.

At this time, the deep learning group training unit 25 may compose at least one low contrast CT image and at least one component CT image, respectively, for each CT image pair of the first training CT dataset, and generate a second training CT dataset using the said composed images. Further, the deep learning group training unit 25 may extract CT exam information from the second training CT dataset and group the second CT data set for training into a plurality of groups according to a predetermined rule. Further, the deep learning group training unit 25 may generate and train a plurality of deep learning models to be trained such that each deep learning model to be trained may correspond to each group of the second training CT dataset. The deep learning group training unit 25 may train each of the plurality of generated deep learning models to be trained.

At this time, the plurality of deep learning models to be trained which has been trained by the deep learning group training unit 25 may refer to a plurality of previously trained deep learning models which is considered in the deep learning model selecting unit 22.

As described above, the deep learning group training unit 25 may train each of the plurality of deep learning models to be trained so as to allow the deep learning model (a deep learning model to be trained) corresponding to a scan attribute of an input CE CT image to output at least one component CT image when the input CE CT image is given as an input.

By doing this, when an input CE CT image is given in this apparatus 20, the deep learning model selecting unit 22 may select a deep learning model among the plurality of previously trained deep learning models corresponding to the scan attribute of the input CE CT image such that the selected deep learning model may operate according to the scan attribute of the input CE CT image, and then the amplified image output unit 24 may output an input CE CT image with an amplified contrast using the selected deep learning model.

As described above, this apparatus 20 may train a plurality of deep learning models (that is, a plurality of deep learning models to be trained) by means of the deep learning group training unit 25 so as to allow the plurality of deep learning models included in this apparatus 20 to output a high contrast CT image with an amplified contrast with respect to a CE CT image input to each deep learning model. Based on the plurality of deep learning models which has been trained in advance (a plurality of deep learning models to be trained which is trained by the training unit), this apparatus 20 may select a corresponding deep learning model from the plurality of previously trained deep learning models in consideration of the exam information extracted from the input CE CT image. Thereafter, this apparatus 20 may enter the input CE CT image to the selected deep learning model as an input to output an input CE CT image with an amplified contrast with respect to the input CE CT image from the selected deep learning model.

The present disclosure may provide a deep learning based CT image contrast amplifying apparatus (apparatuses 10 and 20) which outputs a high contrast CT image (a contrast amplified CT image) from an input CE CT image (for example, a low-concentration contrast media injected CT image) with a low contrast. The input CE CT image with an amplified contrast which is output from these apparatuses 10 and 20 may have a quality which is equal to or higher than that of a normal concentration contrast media injected CT image.

Further, this apparatuses 10 and 20 provide a training (learning) method of the deep learning model (a deep learning model to be trained) to output a contrast amplified CT image from an input CE CT image with a low contrast, with the contrast amplified CT image output by the deep learning model trained as described above (that is, a previously trained deep learning model) having a quality which is equal to or higher than that of the normal concentration contrast media injected CT image.

Further, this apparatuses 10 and 20 train the deep learning model to be trained with the CT data set for training so that when the low contrast CT image (input CE CT image) acquired by the scanning after actually injecting a low concentration contrast medium is used as an input of this apparatuses 10 and 20 (that is, used as an input of at least one deep learning model among the plurality of previously trained deep learning models included in this apparatus), this apparatus may output a contrast amplified CT image with respect to the input low contrast CT image.

This apparatuses 10 and 20 may also be referred to not only as a deep learning based CE CT image contrast amplifying apparatus, but also as a deep learning model (a deep learning model to be trained) training apparatus for amplifying a contrast of a CE CT image based on deep learning. The present disclosure may provide not only a deep learning based CE CT image contrast amplifying method, but also a deep learning model training method for amplifying a contrast of a CE CT image based on deep learning, by means of this apparatuses 10 and 20.

Hereinafter, an operation flow of the present disclosure will be described in brief based on the above detailed description.

Figure 3:
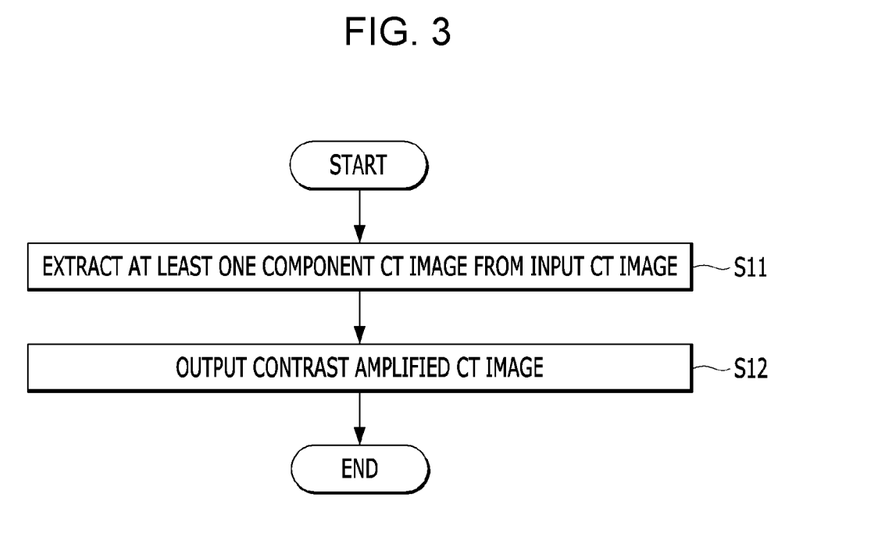
FIG. 3 is a view illustrating a schematic operation flow of a deep learning based CE CT image contrast amplifying method by a deep learning based CE CT image contrast amplifying apparatus according to an exemplary embodiment of the present disclosure.

FIG. 3 is a view illustrating a schematic operation flow of a deep learning based CE CT image contrast amplifying method by means of the deep learning based CE CT image contrast amplifying apparatus according to an exemplary embodiment of the present disclosure.

The deep learning based CE CT image contrast amplifying method illustrated in FIG. 3 may be performed by the above-described deep learning based CE CT image contrast amplifying apparatus (this apparatus, 10). Accordingly, even though description is omitted, the description for the deep learning based CE CT image contrast amplifying apparatus (this apparatus, 10) may also be applied to the description for the deep learning based CE CT image contrast amplifying method in the same manner.

Referring to FIG. 3, in step S11, the image extracting unit 11 may extract at least one component CT image of a CE component and a non-CE component with an input CE CT image as an input of a previously trained deep learning model.

Next, in step S12, the amplified image output unit 12 may output a contrast-amplified CT image with respect to the input CE CT image based on at least one component CT image and the input CE CT image.

At this time, in step S12, the amplified image output unit 12 multiplies the input CE CT image and at least one component CT image extracted in step S11 by each predetermined ratio, respectively, followed by summing of the multiplied results to output a contrast amplified CT image with respect to the input CE CT image.

According to another exemplary embodiment of the present disclosure, in step S12, the amplified image output unit 12 multiplies the input CE CT image and at least one component CT image extracted in step S11 by each predetermined ratio, respectively, followed by summing of the multiplied results to generate a first and second CT images, and applies a predetermined color tone table to the first and second CT image to output a composed color image.

In the meantime, the deep learning based CE CT image contrast amplifying method according to the exemplary embodiment of the present disclosure may include generating and training a deep learning model to be trained before step S11.

Figure 5:
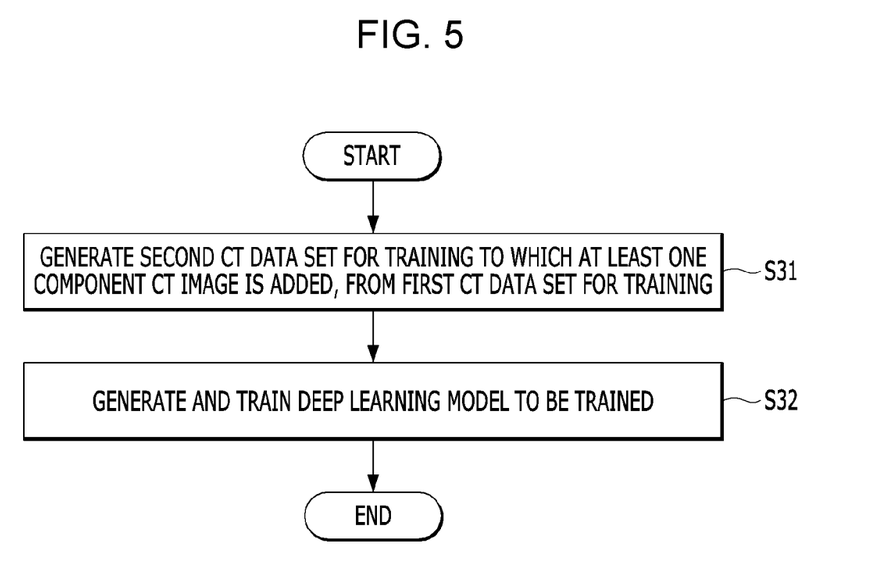
FIG. 5 is a view illustrating an example of a schematic operation flow of a deep learning model training method for amplifying the image contrast of a CE CT image based on deep learning by a deep learning based CE CT image contrast amplifying apparatus according to a first exemplary embodiment of the present disclosure.

At this time, the description of the method for training the deep learning model to be trained, that is, the training method of a deep learning model may be more easily understood with reference to the following FIG. 5.

In the above-description, steps S11 and S12 may be further divided into additional steps or combined as smaller steps depending on an implementation example of the present disclosure. Further, some steps may be omitted if necessary and the order of steps may be changed.

FIG. 5 is a view illustrating an example of a schematic operation flow of a deep learning model training method for amplifying a contrast of a CE CT image based on deep learning by the deep learning based CE CT image contrast amplifying apparatus according to an exemplary embodiment of the present disclosure. That is, FIG. 5 is a view illustrating an example of a schematic operation flow of a method for training a deep learning model to be trained considered in the present disclosure.

The deep learning model training method for amplifying the contrast of a CE CT image based on deep learning illustrated in FIG. 5 may be performed by the above-described deep learning based CE CT image contrast amplifying apparatus (this apparatus, 10). Accordingly, even though description is omitted, the description for the deep learning based CE CT image contrast amplifying apparatus (this apparatus, 10) may also be applied to the description for the deep learning model training method for amplifying the contrast of a CE CT image based on deep learning in the same manner.

Referring to FIG. 5, before the image extracting unit 11 extracts at least one component CT image from an input CE CT image in the above-described step S11 of FIG. 3, the deep learning training unit 13 may generate a second training CT dataset configured by at least one composite low contrast CT image and at least one component CT image of a composite CE component and a composite non-CE component for each CT image pair of the first training CT dataset to train deep learning models included in this apparatus 10.

At this time, the deep learning training unit 13 may compose a CE component CT image and a non-CE component CT image based on the original CT image pair of the first training CT dataset, and compose at least one low contrast CT image based thereon.

At this time, the deep learning training unit 13 may multiply the composed CE component CT image by at least one predetermined ratio, followed by adding the multiplied result to the composed non-CE component CT image to compose at least one low contrast CT image.

Here, the second training CT dataset may be formed of a pair of at least one composite low contrast CT image and at least one composed component CT image obtained based on an original image of the first training CT dataset.

The deep learning training unit 13 may train the deep learning model to be trained using a paired set of at least one composite low contrast CT image and at least one composed component CT image obtained by applying an original image of the first training CT dataset to the image extracting unit 11.

Further, in order to allow the deep learning model to be trained to have a function of extracting at least one component CT image from the input CE CT image thereto in step S11, the deep learning training unit 13 may enter a composite low contrast CT image as an input of the deep learning model to be trained, and repeatedly train the deep learning model to be trained, so as to minimize the difference between the at least one composed component CT image and the output of the deep learning model to be trained.

Figure 4:
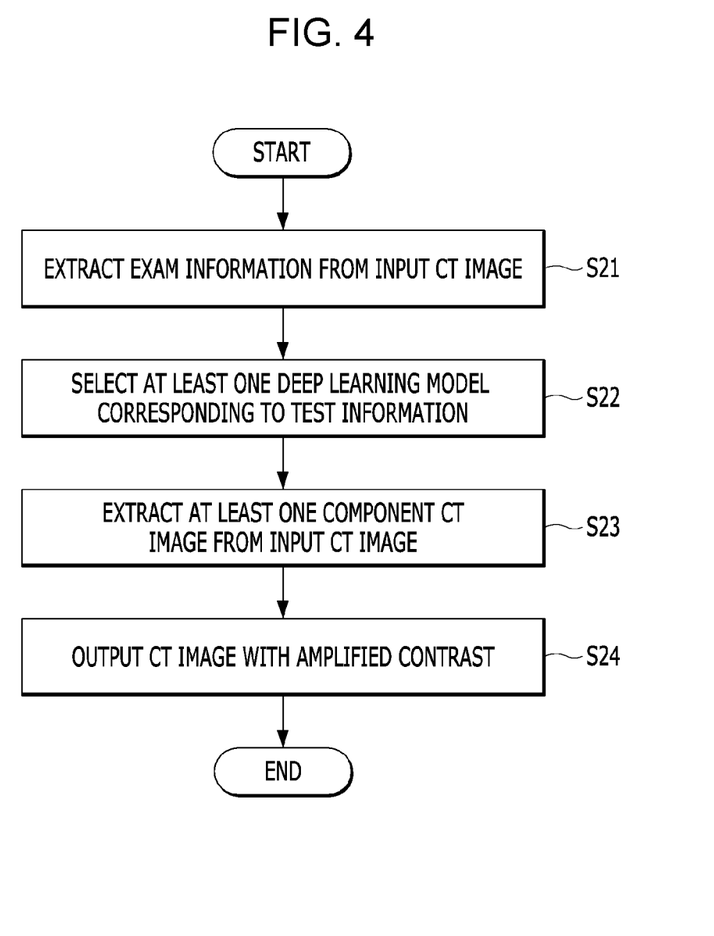
FIG. 4 is a view illustrating a schematic operation flow of a deep learning based CE CT image contrast amplifying method by a deep learning based CE CT image contrast amplifying apparatus according to another exemplary embodiment of the present disclosure.

FIG. 4 is a view illustrating a schematic operation flow of a deep learning based CE CT image contrast amplifying method by the deep learning based CE CT image contrast amplifying apparatus according to another exemplary embodiment of the present disclosure.

The deep learning based CE CT image contrast amplifying method illustrated in FIG. 4 may be performed by the above-described deep learning based CE CT image contrast amplifying apparatus (this apparatus, 20). Accordingly, even though description is omitted, the description for the deep learning based CE CT image contrast amplifying apparatus (this apparatus, 20) may also be applied to the description for the deep learning based CE CT image contrast amplifying method in the same manner.

Referring to FIG. 4, in step S21, the exam information extracting unit 21 may extract CT exam information from an input CE CT image.

Next, in step S22, the deep learning model selecting unit 22 may select at least one deep learning model corresponding to exam information extracted in step S21, among a plurality of previously trained deep learning models.

Next, in step S23, the image extracting unit 23 may extract at least one component CT image with respect to the input CE CT image with the input CE CT image as an input of at least one deep learning model selected in step S22.

Next, in step S24, the amplified image output unit 24 may output a contrast-amplified CT image with respect to an input CE CT image.

In the meantime, the deep learning based CE CT image contrast amplifying method according to the exemplary embodiment of the present disclosure may include generating and training a plurality of deep learning models to be trained before step S21. At this time, the plurality of deep learning models to be trained which is trained by the training may refer to the plurality of previously trained deep learning models which is considered in step S22.

Figure 6:
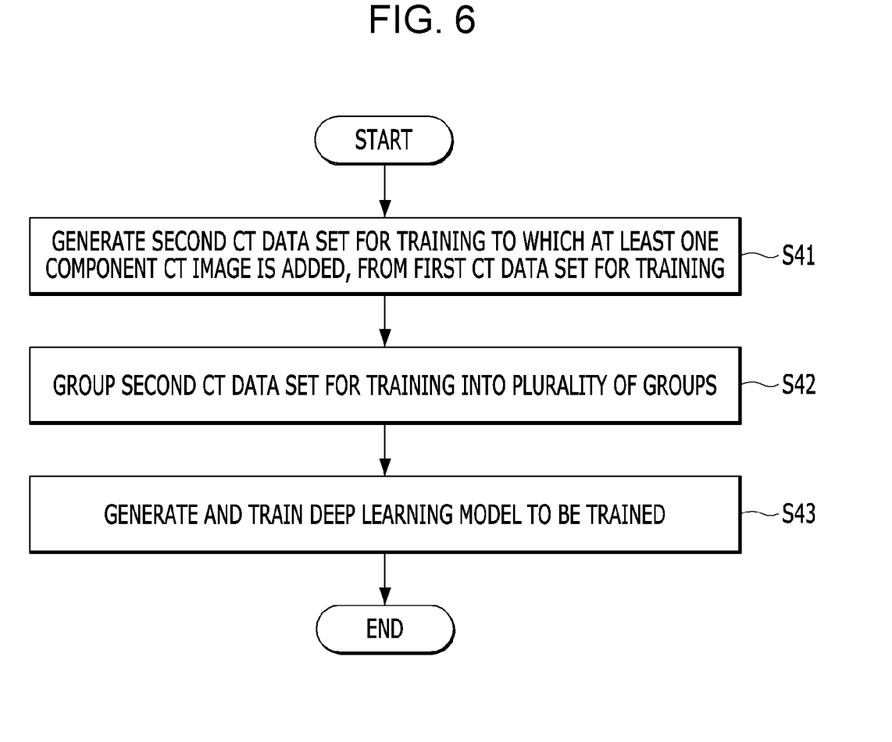
FIG. 6 is a view illustrating an example of a schematic operation flow of a deep learning model training method for amplifying the image contrast of a CE CT image based on deep learning by a deep learning based CE CT image contrast amplifying apparatus according to a second exemplary embodiment of the present disclosure.

In this case, the description of the method for training the plurality of deep learning models to be trained, that is, the training method of a deep learning model may be more easily understood with reference to the following FIG. 6.

In the above-description, steps S21 to S24 may be further divided into additional steps or combined as smaller steps depending on an implementation example of the present disclosure. Further, some steps may be omitted if necessary and the order of steps may be changed.

FIG. 6 is a view illustrating an example of a schematic operation flow of the deep learning model training method for amplifying a contrast of a CE CT image based on deep learning by means of the deep learning based CE CT image contrast amplifying apparatus according to an exemplary embodiment of the present disclosure. That is, FIG. 6 is a view illustrating an example of a schematic operation flow of a method for training the deep learning model to be trained considered in the present disclosure.

The deep learning model training method for amplifying the image contrast of a CE CT image based on deep learning illustrated in FIG. 6 may be performed by the above-described deep learning based CE CT image contrast amplifying apparatus (this apparatus, 20). Accordingly, even though description is omitted, the description for the deep learning based CE CT image contrast amplifying apparatus (this apparatus, 20) may also be applied to the description for the deep learning model training method for amplifying the image contrast of a CE CT image based on deep learning in the same manner.

Referring to FIG. 6, in step S41, the deep learning group training unit 25 may compose at least one component CT image and at least one low contrast CT image based on the first training CT dataset and generate a second training CT dataset using the composed image, to train deep learning models included in this apparatus 20, before the exam information extracting unit 21 extracts exam information from the input CE CT image in the above-described step S21 of FIG. 4.

The deep learning group training unit 25 may train a deep learning model to be trained using a paired set of at least one composite low contrast CT image and at least one composed component CT image.

Next, in step S42, the deep learning group training unit 25 may extract CT exam information from the second training CT dataset, and group the second training CT dataset into a plurality of groups according to a predetermined rule.

At this time, in step S42, the deep learning group training unit 25 groups the second training CT dataset into a plurality of groups to generate CT datasets for training for different body parts and/or scan attributes.

Next, in step S43, the deep learning group training unit 25 may generate and train a plurality of deep learning models to be trained such that each deep learning model to be trained may correspond to each group of the second training CT dataset generated in step S42.

Specifically, in step S43, the deep learning group training unit 25 may generate and train a deep learning model to be trained for different body parts corresponding to each CT data set for training generated for different body parts. Further, the deep learning group training unit 25 may generate and train the deep learning models to be trained for different scan attributes corresponding to the CT data set for training generated for different scan attributes.

In step S43, the deep learning group training unit 25 may train a plurality of deep learning models to be trained generated in step S42 using the plurality of CT data sets for training (that is, a plurality of CT dataset groups for training) generated in step S42.

As a specific example, in step S43, the deep learning group training unit 25 may train each deep learning model to be trained for different body parts and/or scan attributes generated in step S43 using the CT dataset for training generated for different body parts and/or the scan attributes in step S42, so as to correspond thereto.

Further, in step S43, in order to allow the plurality of deep learning models to be trained to have a function of extracting at least one component CT image from the CE CT image input thereto, the deep learning group training unit 25 may enter a composite low contrast CT image as an input of each deep learning model to be trained for each CT image pair in the corresponding second training CT dataset, respectively, for every group grouped in step S42 and repeatedly train the deep learning model to be trained so as to minimize the difference between the at least one composed component CT image and an output of the deep learning model to be trained.

In one exemplary embodiment of the present disclosure, the deep learning group training unit 25 may repeatedly train each of the deep learning models to be trained generated for different body parts using the CT dataset for training generated for different body parts in step S43.

In another exemplary embodiment of the present disclosure, the deep learning group training unit 25 may repeatedly train each of the deep learning models to be trained generated for different scan attributes using the CT dataset for training generated for different scan attributes in step S43.

By doing this, the plurality of deep learning models to be trained considered in this apparatus 20 may include a deep learning model to be trained generated for different body parts and a deep learning model to be trained generated for different scan attributes.

In the above-description, steps S41 to S43 may be further divided into additional steps or combined as smaller steps depending on an implementation example of the present disclosure. Further, some steps may be omitted if necessary and the order of steps may be changed.

The deep learning based CE CT image contrast amplifying method and the deep learning model training method for amplifying a contrast of a CE CT image based on deep learning according to the exemplary embodiment of the present disclosure may be implemented in the form of a program instruction which can be executed by various computer units to be recorded in a computer readable medium. The computer readable medium may include solely a program instruction, a data file, and a data structure or a combination thereof. The program instruction recorded in the medium may be specifically designed or constructed for the present invention or known to those skilled in the art of a computer software to be used. Examples of the computer readable recording medium include magnetic media such as a hard disk, a floppy disk, or a magnetic tape, optical media such as a CD-ROM or a DVD, magneto-optical media such as a floptical disk, and a hardware device which is specifically configured to store and execute the program instruction, such as a ROM, a RAM, and a flash memory. Examples of the program instruction include not only a machine language code which is created by a compiler but also a high level language code which may be executed by a computer using an interpreter. The hardware device may operate as one or more software modules in order to perform the operation of the present invention and vice versa.

Further, the above-described deep learning based CE CT image contrast amplifying method and the deep learning model training method for amplifying a contrast of a CE CT image based on deep learning may be implemented in the form of a computer program or an application executed by a computer which is stored in a recording medium.

The above-description of the present disclosure is illustrative only and it is understood by those skilled in the art that the present disclosure may be easily modified to another specific type without changing the technical spirit of an essential feature of the present disclosure. Thus, it is to be appreciated that the embodiments described above are intended to be illustrative in every sense, and not restrictive. For example, each component which is described as a singular form may be divided to be implemented and similarly, components which are described as a divided form may be combined to be implemented.

The scope of the present disclosure is represented by the claims to be described below rather than the detailed description, and it is to be interpreted that the meaning and scope of the claims and all the changes or modified forms derived from the equivalents thereof come within the scope of the present disclosure.

What is claimed is:

1. A deep learning based contrast-enhanced computer tomographic (CE CT) image contrast amplifying method, comprising:
   extracting at least one component CT image between a contrast-enhanced (CE) component and a non-CE component for an input CE CT image with the input CE CT image as an input to a previously trained deep learning model; and
   outputting a contrast-amplified CT image with respect to the input CE CT image based on the input CE CT image and the at least one extracted component CT image,
   wherein the previously trained deep learning model is a deep learning model which is trained by:
   composing at least one component computer tomographic (CT) image dataset based on an image pair of a first training CT dataset;
   generating a second training CT dataset based on the said at least one composed component CT image dataset and the first training CT dataset; and
   generating and training a deep learning model to be trained, in advance, using the second training CT dataset to extract the at least one component CT image.

2. The deep learning based CE CT image contrast amplifying method according to claim 1, further comprising:
   before the extracting of at least one component CT image, extracting exam information from the input CE CT image; and
   selecting at least one deep learning model corresponding to the exam information, among a plurality of previously trained deep learning models,
   wherein the extracting of at least one component CT image includes:
   extracting the at least one component CT image with respect to the input CE CT image with the input CE CT image as an input to at least one selected deep learning model.

3. The deep learning based CE CT image contrast amplifying method according to claim 2, further comprising:
   before the extracting of exam information,
   composing at least one component CT image based on an image pair of a first training CT dataset;
   generating a second training CT dataset based on the dataset of the said at least one composed component CT image and the first training CT dataset;
   extracting the exam information from the second training CT dataset and grouping the second training CT dataset into a plurality of groups according to a predetermined rule; and
   generating and training a plurality of deep learning models to be trained such that each deep learning model to be trained may correspond to each group of the second training CT dataset,
   wherein in the selecting, the plurality of previously trained deep learning models is the plurality of deep learning models to be trained which is trained by the training.

4. The deep learning based CE CT image contrast amplifying method according to claim 1, wherein the outputting of a contrast-amplified CT image includes:
   multiplying the input CE CT image and the at least one component CT image by each predetermined ratio, respectively, followed by summing of the multiplied results.

5. The deep learning based CE CT image contrast amplifying method according to claim 1, wherein the outputting of a contrast-amplified CT image includes:
   generating a first CT image and a second CT image by multiplying the input CE CT image and the at least one component CT image by each predetermined ratio, respectively, followed by summing of the multiplied results; and
   outputting a composed color image by applying a predetermined color tone table to the first CT image and the second CT image.

6. A deep learning based contrast-enhanced computer tomographic (CE CT) image contrast amplifying apparatus, comprising:
   a deep learning training unit which generates and trains a deep learning model to be trained,
   an image extracting unit which extracts at least one component computer tomographic (CT) image between a contrast-enhanced (CE) component and a non-CE component for an input CE CT image with the input CE CT image as an input to a previously trained deep learning model; and an amplified image output unit which outputs a contrast-amplified CT image with respect to the input CE CT image based on the input CE CT image and the at least one extracted component CT image, wherein the deep learning training unit composes at least one component CT image dataset based on an image pair of a first training CT dataset; generates a second training CT dataset based on the said at least one composed component CT image dataset and the first training CT dataset; and generates and trains a deep learning model to be trained, in advance, using the second training CT dataset, to extract the at least one component CT image, and the previously trained deep learning model is a deep learning model which is trained by the deep learning training unit.

7. The deep learning based CE CT image contrast amplifying apparatus according to claim 6, further comprising:

an exam information extracting unit which extracts exam information from the input CE CT image; and a deep learning model selecting unit which selects at least one deep learning model corresponding to the exam information, among a plurality of previously trained deep learning models, wherein the image extracting unit inputs the input CE CT image to at least one deep learning model selected by the exam information extracting unit and the deep learning model selecting unit to extract the at least one component CT image with respect to the input CE CT image.

8. The deep learning based CE CT image contrast amplifying apparatus according to claim 7, further comprising:

a deep learning group training unit which generates and trains a plurality of deep learning models to be trained, wherein the deep learning group training unit composes at least one component CT image based on an image pair of a first training CT dataset; generates a second training CT dataset based on the dataset of the said at least one composed component CT image and the first training CT dataset; and extracts exam information from the second training CT dataset and groups the second training CT dataset into a plurality of groups according to a predetermined rule, and generates and trains the plurality of deep learning models to be trained such that each deep learning model to be trained may correspond to each group of the second training CT dataset, and the plurality of previously trained deep learning models is the plurality of deep learning models to be trained which is trained by the deep learning group training unit.

9. The deep learning based CE CT image contrast amplifying apparatus according to claim 6, wherein the amplified image output unit multiplies the input CE CT image and the at least one component CT image by each predetermined ratio, respectively, followed by summing of the multiplied results.

10. The deep learning based CE CT image contrast amplifying apparatus according to claim 6, wherein the amplified image output unit multiplies the input CE CT image and the at least one component CT image by each predetermined ratio, respectively, followed by summing of the multiplied results to generate a first CT image and a second CT image, and applies a predetermined color tone table to the first CT image and the second CT image to output a composed color image.

* * * * *